Figure 1:
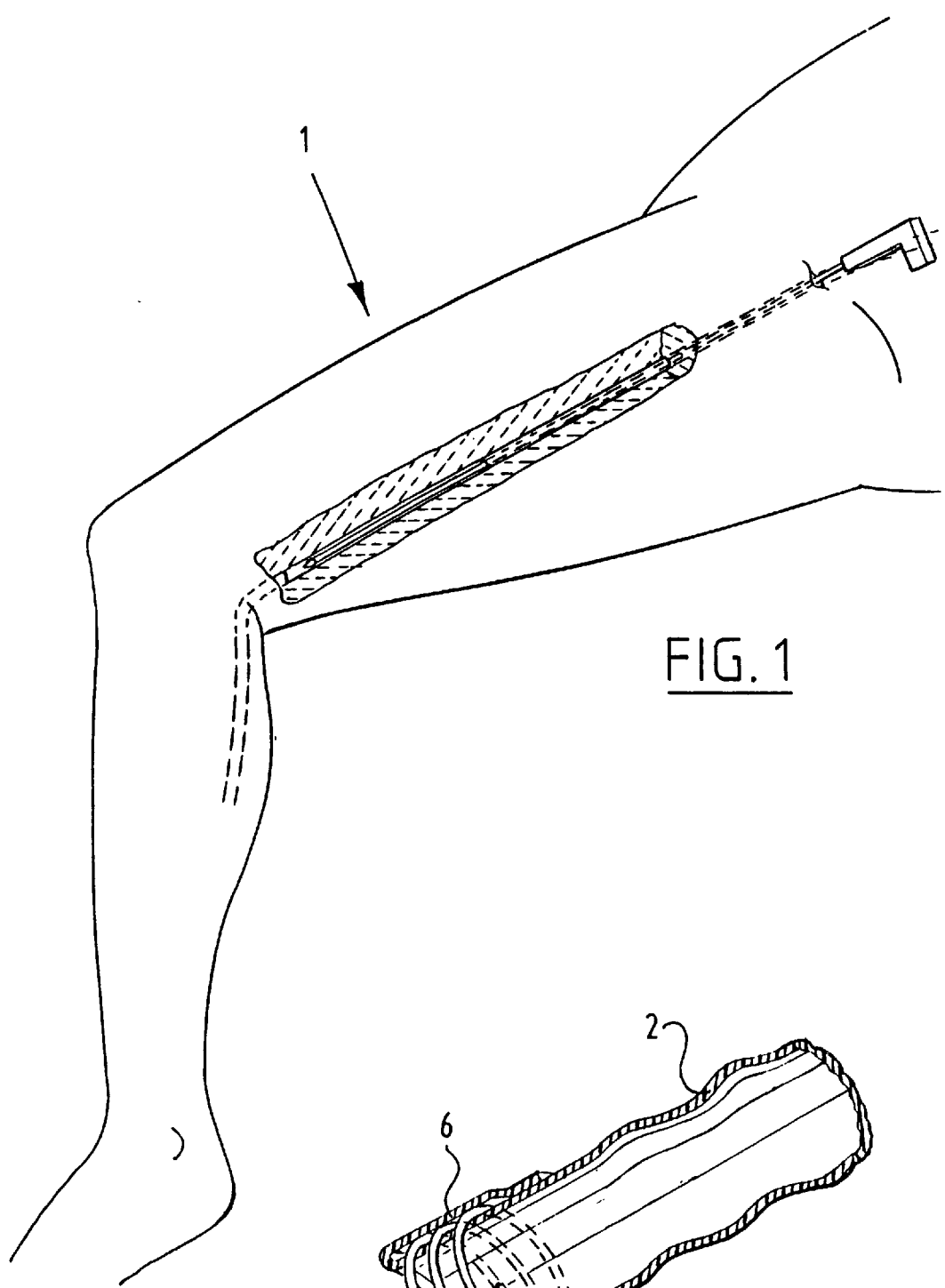

United States Patent
Kalmann et al.

[11] Patent Number: 5,879,380
[45] Date of Patent: Mar. 9, 1999

[54] ASSEMBLY FOR TREATING BLOOD VESSELS AND A METHOD THEREFOR

[75] Inventors: Menno Kalmann, Elspeet; Franciscus Laurens Moll, La Bosch en Duin, both of Netherlands

[73] Assignee: Medtronic, Inc., Minneapolis, Minn.

[21] Appl. No.: 809,630

[22] PCT Filed: Oct. 4, 1995

[86] PCT No.: PCT/NL95/00336

§ 371 Date: Jun. 27, 1997

§ 102(e) Date: Jun. 27, 1997

[87] PCT Pub. No.: WO96/10375

PCT Pub. Date: Apr. 11, 1996

[30] Foreign Application Priority Data

Oct. 4, 1994 [NL] Netherlands .......................... 9401633

[51] Int. Cl.$^6$ .................................................. A61F 2/06
[52] U.S. Cl. ................................................ 623/1; 128/898
[58] Field of Search ............................ 606/194, 195; 623/1

[56] References Cited

U.S. PATENT DOCUMENTS 4,665,918  5/1987  Garza et al. .
5,360,443  11/1994  Barone et al. ............................ 606/194
5,480,423  1/1996  Ravenscroft et al. ................... 606/194
5,522,881  6/1996  Lentz .
5,603,721  2/1997  Lau et al. ................................. 606/194
5,662,700  9/1997  Lazarus .................................... 606/194

FOREIGN PATENT DOCUMENTS 0 119 688  9/1984  European Pat. Off. .
0 274 846  7/1988  European Pat. Off. .
WO 90/01969  3/1990  WIPO .
WO 94/04096  3/1994  WIPO .

*Primary Examiner*—David J. Isabella
*Attorney, Agent, or Firm*—Townsend and Townsend and Crew LLP

[57] ABSTRACT

The invention relates to a blood vessel treating assembly including an artificial blood vessel inner layer such as an artificial tunica-intima for replacing a section of blood vessel inner layer previously removed from a blood vessel and/or for covering a predetermined length of a damaged blood vessel inner layer. The artificial blood vessel inner layer is associated with the existing blood vessel in such a way as to substanitially stop any loose parts of the blood vessel from obstructing the stream of blood through the blood vessel. A novel method for introducing the the artificial blood vessel inner layer into the blood vessel is also disclosed.

20 Claims, 5 Drawing Sheets

ASSEMBLY FOR TREATING BLOOD VESSELS AND A METHOD THEREFOR

This invention relates to an assembly for the treating of blood vessels and more specifically to an assembly for the replacing of and/or covering up of damaged, blood vessel inner layers and to a method therefor.

An often occurring medical problem is the silting up of blood vessels with for instance calcium, so-called arteriosclerosis. Because of this, a blockage of the blood vessel occurs, so-called stenosis.

Stenosis of blood vessels which leads to a narrowing and, in some cases, complete blocking of the blood vessel can lead to dangerous consequences for the patient. Circulatory problems and a deteriation in health can ensue. Advanced stenosis, if not operated upon, can cause wastage and death of body tissue, necessitating, in certain instances, in amputation.

A known procedure for unblocking blood vessels, 'End artery ectomy', is to separate the inner layer of the blood vessel, the so called tunica-intima, from the blood vessel wall, to cut through and sever the tunica-intima over the blocked length of the bloodvessel and then to remove the tunica-intima plus blockage from the body. A new tunica-intima then grows back to replace this removed tunica-intima.

A problem here is that this new tunica-intima, the so called neo-tunica-intima has the tendency to undergo restenosis, i.e. to silt up again, at a quicker rate than the original tunica-intima.

Another problem is that the original tunica-intima is usually separated from the blood vessel wall upto a distance just past where it is to be severed. Hence on removal of the original tunica-intima, a small piece of this is left hanging loosely in the blood stream, a factor which can cause and hasten the restenosis of the blood vessel.

A blood vessel which is particularly susceptible to stenosis is the artery between the groin and the knee.

It is an object of the present invention to obviate at least one of these problems. To this end there is provided, according to a first aspect of the present invention, a blood vessel treating assembly comprising:

an artificial blood vessel inner layer such as an artificial tunica-intima or the like for replacing a section of blood vessel inner layer previously removed from the blood vessel and/or for covering a predetermined length of damaged blood vessel inner layer, wherein said artificial blood vessel inner layer is associated with the existing blood vessel in such a way as to substantially withhold any loose parts of the blood vessel from obstructing the stream of blood through said blood vessel, and introducing means for introducing the artificial blood vessel inner layer into the blood vessel.

In this way an artificial new tunica-intima to replace the old tunica-intima over the removed length thereof and which prevents the re-growing of a natural 'neo-tunica-intima', can be introduced into a blood vessel, to just past the piece of loose hanging original tunica-intima left after removal of a section of the original tunica-intima for instance, this artificial new tunica-intima made of such material as to cause a minimum of restenosis of the blood vessel to occur and which pushes the old loose hanging piece of left behind tunica-intima back against the blood vessel wall where it re-grows onto the blood vessel wall and thus no longer flaps about in the blood stream.

According to a second aspect of the present invention there is provided an artificial blood vessel inner layer, such as an artificial tunica-intima or the like, made of any suitable synthetic material and comprising diameter arranging means for increasing and/or decreasing the diameter of the tube-like section, preferably for use with the above mentioned assembly.

According to a third aspect of the present invention there is provided introducing means for introducing an artificial blood vessel inner layer, such as an artificial tunica-intima or the like, into a blood vessel, preferably for use with the assembly and/or the artificial blood vessel inner layer as mentioned above.

According to a fourth aspect of the present invention there is provided a method of replacing a previously removed inner layer of a blood vessel and/or for covering a predetermined length of damaged blood vessel inner layer comprising the steps of inserting a blood vessel treating assembly as mentioned above, via an incision, upto a predetermined distance into a blood vessel, increasing the diameter of the artificial blood vessel inner layer to push against the blood vessel walls, whereafter the introducing means are removed and joining the end of the artificial blood vessel inner layer to the existing blood vessel near the incision.

According to a fifth aspect of the present invention there is provided a method of increasing and/or decreasing the diameter of a length of artificial blood vessel inner layer, as mentioned above, or the like, comprising bringing a length of memory metal associated with the artificial blood vessel inner layer to its preprogrammed activation temperature whereafter expansion/contraction of the memory metal effectively increases/decreases the diameter of the length of artificial blood vessel inner layer.

According to a further aspect of the present invention there is provided an assembly comprising a tube-like section with at least one length of memory metal associated therewith, pre-programmed to assume a desired form and/or expand and/or contract at a pre-determined activation temperature, and introducing means for introducing the tube-like section into a passage-like area.

Figure 2:
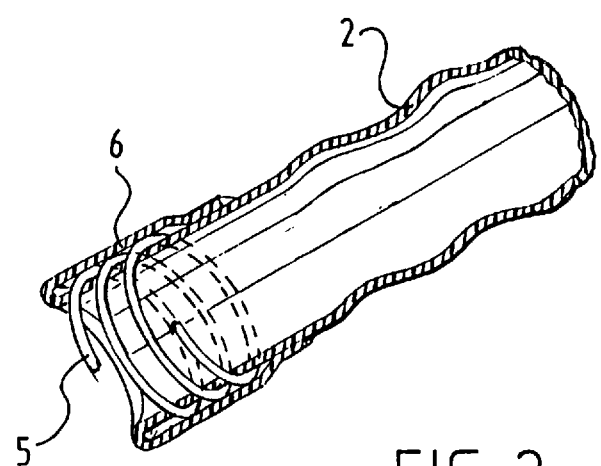
Figure 3:
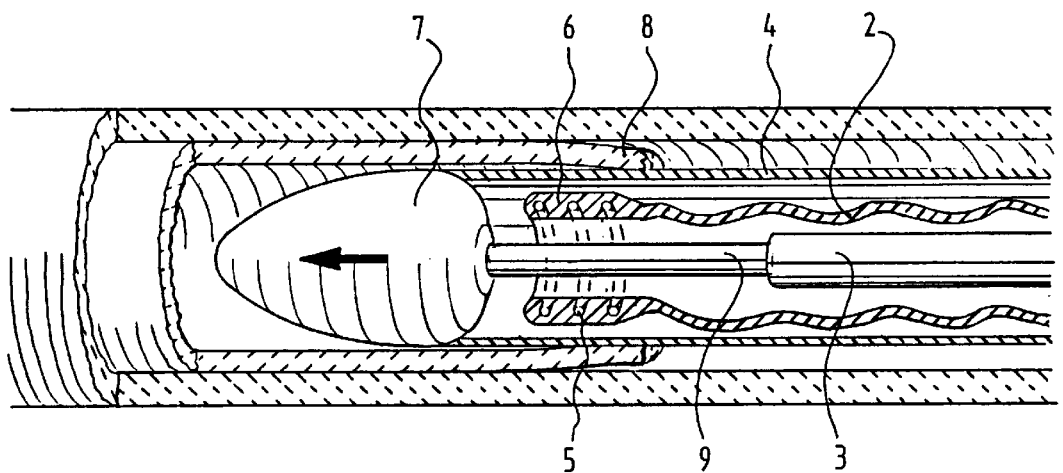
Figure 7:
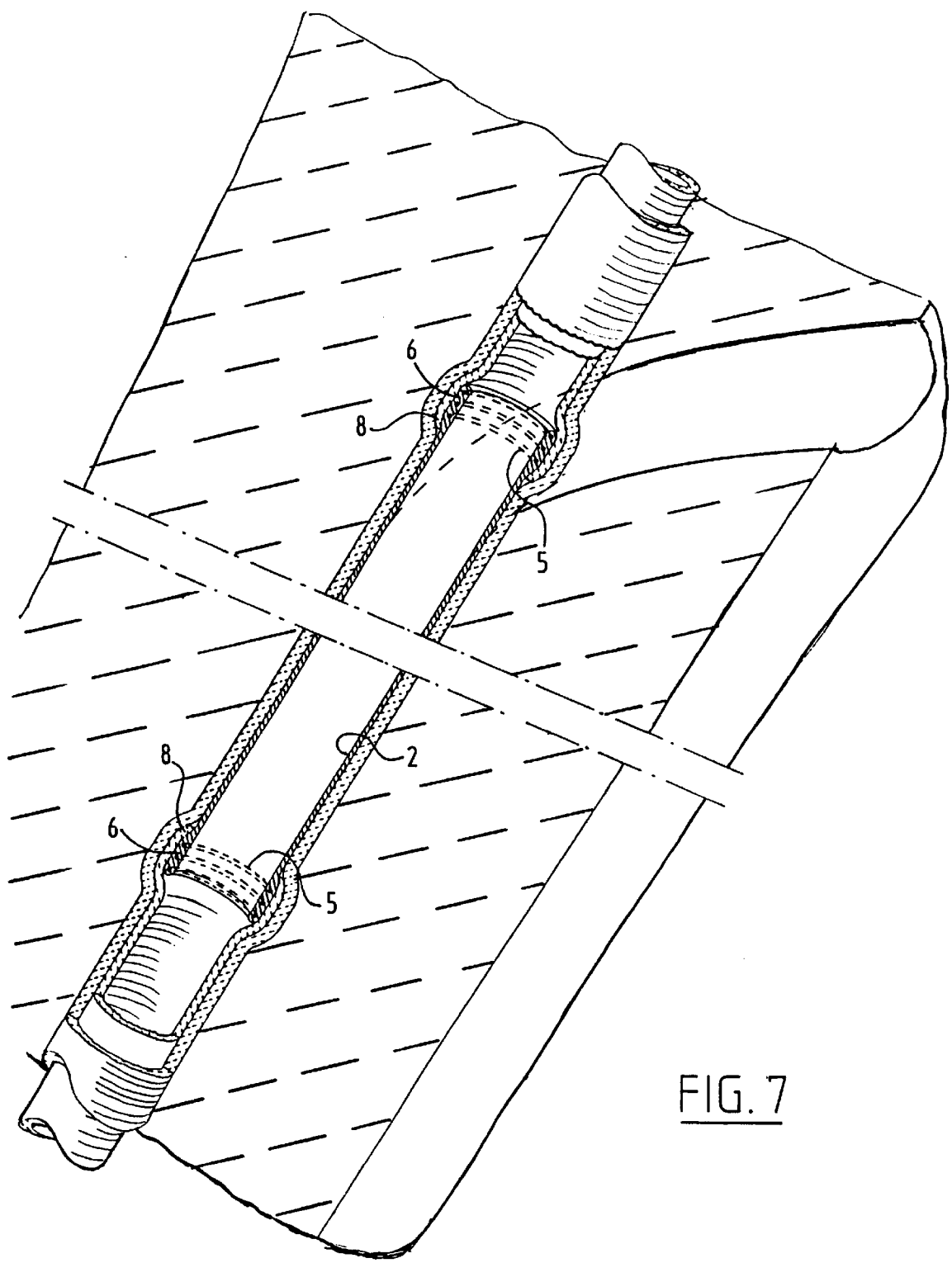

Further advantages, characteristics and details of the present invention will become clear from the following description with reference to the accompanying drawings which show:

FIG. 1 a perspective partly cut away view of a preferred embodiment of the assembly according to the present invention, during introduction into the artery between the groin and the knee;

FIG. 2 a partly cut away perspective view of the artificial blood vessel inner layer of the assembly from FIG. 1;

FIGS. 3 to 6 partly cut away perspective views showing the succesive steps of the assembly from FIG. 1 carrying out introduction of the artificial blood vessel inner layer from FIG. 2, into a blood vessel;

FIG. 7 a partly cut away perspective view of an embodiment of the artificial blood vessel inner layer according to the present invention, when in position within a blood vessel.

Figure 8:
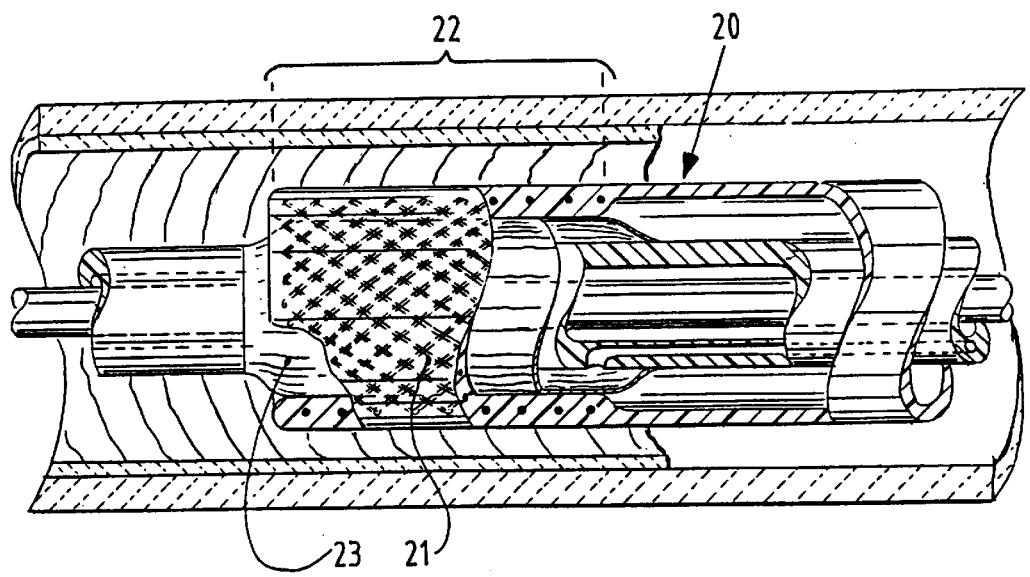
Figure 9:
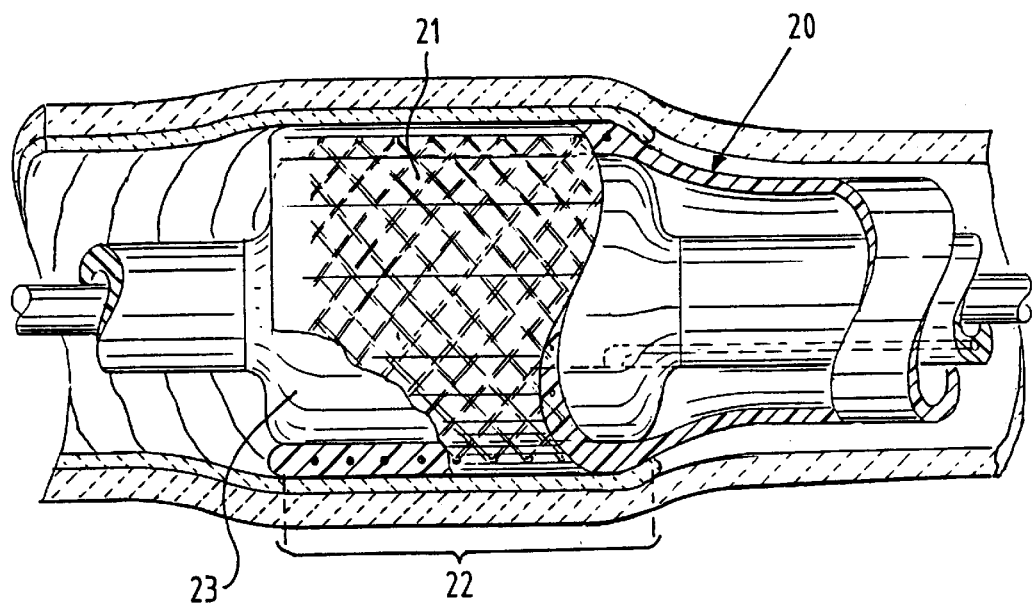

FIGS. 8 to 9 partly cut away perspective views of a second embodiment of the present invention.

The assembly 1 (FIG. 1) is introduced into the artery between the groin and the knee, for example, preferably via an incision already made for the removal of the original tunica-intima plus blockage.

This yields the advantage that further incisions for introduction of the assembly into the blood vessel need not be made into the patient, which in turn yields the benefits of reduced stress on the patient, reduced operation and recovery time and accordingly low hospital costs.

The assembly 1 comprises an artificial blood vessel inner layer 2 (see FIGS. 2 to 7) and introducing means for introducing the artificial blood vessel inner layer into the blood vessel.

The introducing means preferably comprise a catheter-like element 3 (see FIGS. 1, 3–6) which is preferably operated from outside of the body (see FIG. 1).

The artificial blood vessel inner layer 2 (FIGS. 2–7), which preferably takes the form of a blood vessel tunica-intima, comprises a tube-like section of synthetic material.

A protective cover is preferably associated with the assembly 1, this preferably taking the form of a removeable sheath 4 (FIGS. 3, 4) which extends from the front of the assembly 1 to the catheter operator.

This protective sheath 4 ensures that minimal damage is incurred to the blood vessel wall during introduction of the assembly 1 and that the artificial tunica-intima 2 is substantially protected from any possible interferences which could hinder introduction.

Diameter arranging means are preferably associated with the tube-like section of synthetic material, said diameter arranging means preferably being a length of preprogrammed memory metal 5 (FIGS. 2–7). These diameter arranging means are often referred to as a "stent".

The tube-like section of the artificial tunica-intima 2 is preferably folded over at its leading end (see FIGS. 2–6), the resulting fold 6 of for example 2 cm preferably enclosing the length of memory metal 5 which preferably takes the form of a coil.

The artificial tunica-intima 2 is preferably made of a fluoro carbon polymer, by choice the polymer which goes under the name of teflon, a trademarked name, of Du Pont. Clinical tests have shown that teflon is efficient in ensuring a minimum restenosis of blood vessels.

The fact that the coil of memory metal 5 is enclosed as it were in the fold 6 of the artificial tunica-intima 2, means that the memory metal 5 does not come into direct contact with either the blood vessel or the blood stream, so that calcium or any other such blood vessel blocking material is not given a 'foot-hold', on the memory metal, on which it could remain, a factor which further reduces restenosis and/or the rate at which restenosis occurs.

For example, the coil of memory metal can be preprogrammed to increase from a diameter of about 2 mm at room temperature to a diameter of about 8 mm at a temperature of about 35° C. in the blood vessel.

The fact that the length of memory metal is preferably in the form of a coil, ensures that a uniform expansion/contraction of the artificial tunica-intima occurs when the preprogrammed temperature of the memory metal is reached.

In use the assembly is inserted into the blood vessel via an incision already made (see FIG. 1). A guiding wire (not shown) can be introduced into the blood vessel, before introduction of the assembly 1, whereafter the assembly 1 can be pushed over this guiding wire and through the blood vessel.

Blood vessel widening means, for widening the blood vessel during introduction of the assembly, bunging means for blocking off the passage of blood into the assembly during introduction of the assembly into the blood vessel, which could cause introduction complications, and pressure exerting means for pushing the introduced artificial tunica-intima against the blood vessel walls when in position, are preferably associated with the assembly, and preferably take the form of a cone-like element 7 mounted on the front of the catheter-like element 3 (see FIGS. 3–6).

The cone-shape of the cone-like element 7 enables the assembly 1 to easily follow the passage of the blood vessel, pushing the blood vessel walls apart as it goes in order to facilitate introduction of the assembly 1.

During introduction of the assembly 1, the cone-like element 7 is pushed to a point just past were the old tunica-intima was severed so that the fold 6 of the artificial tunica-intima 2 is encircled by the loose hanging remaining piece of the original tunica-intima 8 (see FIGS. 3–7). At this point forward movement of the assembly 1 is stopped.

Figure 4:
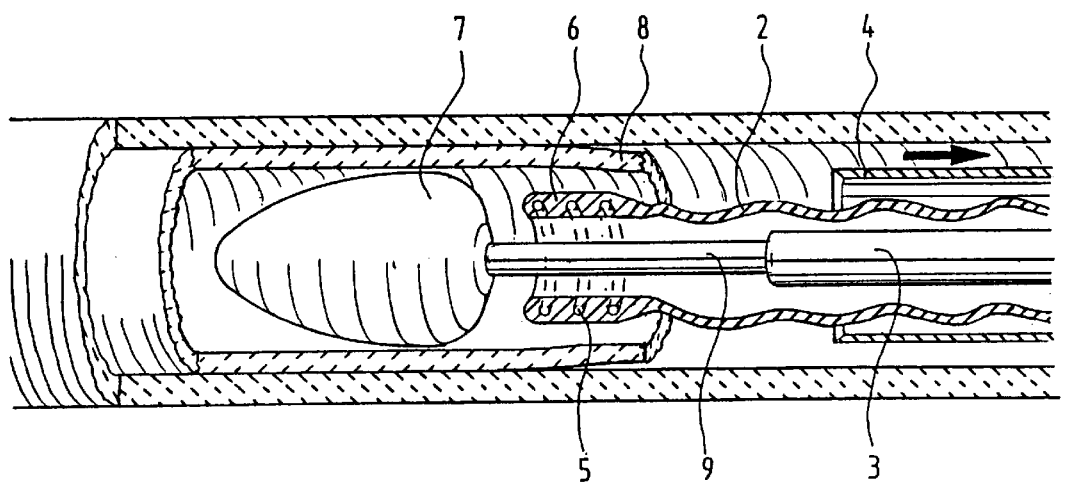

The protective sheath 4 is then pulled back off the assembly 1 whilst the assembly 1 itself is held in position (FIG. 4). The artificial tunica-intima 2, still in its small diameter state, at this point in time, is relatively tightly wrapped around the catheter-like element 3 (see FIG. 4).

During withdraw of the protective sheath 4, it was found during clinical tests that the artificial tunica-intima 2 sometimes had the inclination to be pulled back along the catheter-like element 3 together with the sheath 4. In order to prevent this, the catheter-like element 3 can be locally given a somewhat smaller diameter 9 at the position where the memory metal coil 5 is associated with the fold 6 (see FIGS. 3–6), so that the fold 6 and coil of memory metal 5 remain secured in the desired position on withdrawal of the protective sheath 4.

A further feature of the protective sheath is that it aids in insulating the coil of memory metal from the temperature in the blood vessel during introduction of the assembly, so that the coil does not assume its preprogrammed shape until reaching its activation temperature which occurs when the sheath is withdrawn. This prevents the coil from expanding at an undesired position within the blood vessel.

Figure 5:
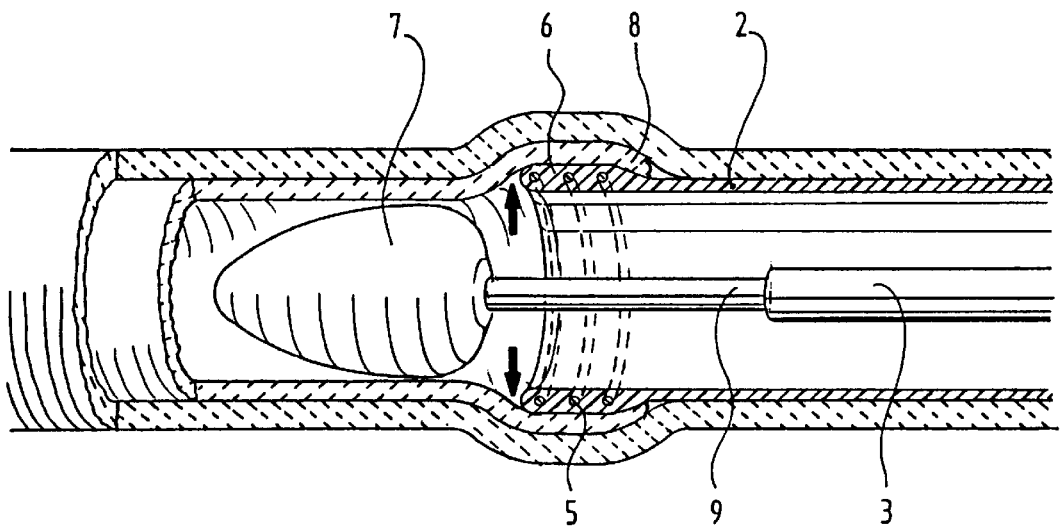

A short period after withdrawal of the protective sheath the coil of memory metal 5 reaches its activation temperature, whereupon the coil of memory metal 5 increases in diameter and so doing pushes the artificial tunica-intima 2 against the walls of the blood vessel (see FIG. 5).

Figure 6:
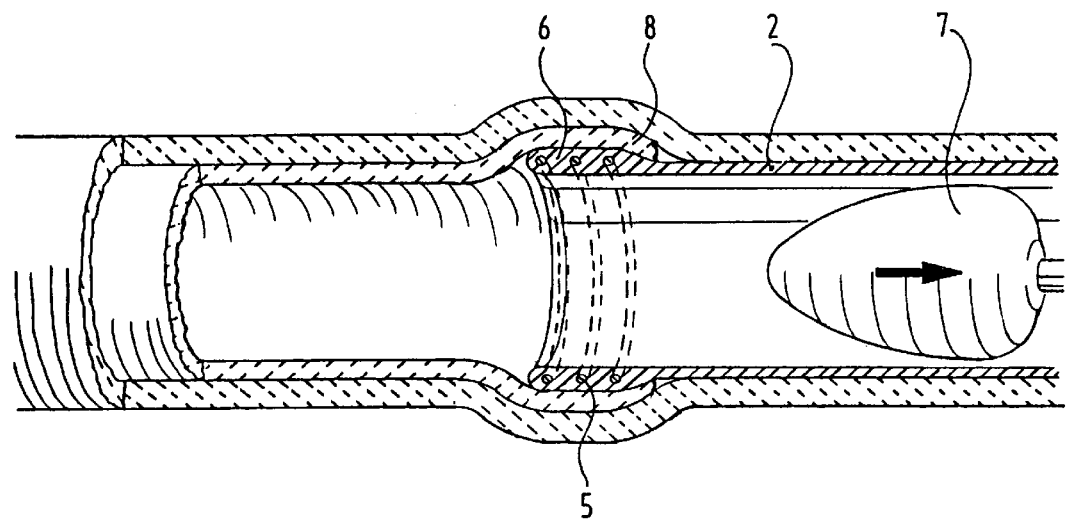

The artificial tunica-intima 2 pushes the loose hanging piece of remaining old tunica-intima 8 into the blood vessel wall so that this no longer flaps around in the blood stream (see FIGS. 5–7).

The diameter of the artificial tunica-intima 2 is now large enough for the catheter-like element 3, plus the cone-like element 7 to be withdrawn out of the blood vessel, the cone-like element 7 further exerting a certain pressure on the artificial tunica-intima 2 during this withdrawal to further open out and push the latter somewhat into the blood vessel wall (see FIG. 6).

According to the present invention, it is not necessary to support the artificial tunica-intima over its whole length, whereby unnecessary added pressure is exerted against the blood vessel wall. The artificial tunica-intima, once in place, is held in position by the blood pressure.

After removal of the sheath 4 and the catheter-like element 3, the artificial tunica-intima 2 can be joined to the blood vessel wall near the incision, preferably by means of stitches. However as shown in FIG. 7 another possibility to secure the artificial tunica-intima in position within the blood vessel is to equip the artificial tunica-intima with a further coil of memory metal so that the both ends of the artificial section of tunica-intima are forced against blood vessel wall.

After a period of time the artificial tunica-intima grows onto the original blood vessel wall.

It will be obvious that during sterilisation, before introduction of the assembly, the memory metal coil should be temporarily held in its small diameter state, by means of for instance a collar, so that it does not assume its preprogrammed expanded form at this stage.

A further embodiment of the present invention is shown in FIGS. 8 and 9.

In this embodiment 20, the length of preprogrammed memory metal, is replaced by a section of gauze-like material 21 (FIGS. 8 and 9), enclosed within an end section 22 of the artificial tunica-intima.

The end section 22 and artificial intima-tunica are pushed over an expandible balloon 23 and a protective sheath, not shown, is brought thereover. Following introduction, the sheath is removed and the balloon 23 expanded to force the end section 22 against the wall of the blood vessel, whereby it is held in position by the stent 21, to affix with the blood vessel wall. Blood pressure forces the length of unsupported artificial intima-tunica to affix with the blood vessel wall as in the first embodiment. Following positioning, the balloon 23 is removed.

This stent 21 is preferably made from stainless steel.

The artificial tunica-intima is required to be supple, and have elastic and anti-thrombogenic qualities and is preferably porous, in order to mimic the qualities of the tunica-intima. A suitable material herefor is polytetrafluorethylene made by Dacron.

The material for the artificial tunica-intima can be supplied with endothelial cells in order to further enhance its working as a tunica-intima.

Although the present invention refers to the introduction and placing of an artificial intima tunica, intima tunicas from the patient self and from donors may be introduced and arranged in position according to the present invention.

The present invention thus yields a simple yet efficient introduction of a new artificial inner blood vessel layer, which can be carried out in a short time and with a minimum of discomfort to the patient.

The present invention is not limited to the hereabove described and illustrated embodiments, rather within the range of the following claims, a large number of modifications and variations are conceivable.

We claim:

1. A method for replacing a section of blood vessel inner layer comprising the steps of:

forming an incision into the blood vessel;

removing a section of an inner layer of a blood vessel through the incision, wherein the removal creates at least one end flap in a remaining blood vessel inner layer;

providing an artificial blood vessel inner layer comprising a supple tubular section having inner and outer surfaces, at least one end section of said tubular section folded back over said outer surface creating an enclosure, and a stent enclosed within said enclosure;

inserting the stented end of said artificial inner layer into said blood vessel through the incision in the direction of blood flow;

positioning said artificial inner layer within said blood vessel so that said end section enclosing said stent is positioned adjacent said end at a downstream location from said incision flap; and retaining said end flap between said end section and said blood vessel by expanding said stent.

2. A method as in claim 1, wherein said providing step comprises providing an artificial blood vessel inner layer having a tubular section comprising a fluoro carbon polymer.

3. A method as in claim 1, wherein said providing step comprises providing an artificial blood vessel inner layer having a tubular section that has a length at least as long as said removed section of blood vessel inner layer.

4. A method as in claim 1, wherein said providing step comprises providing an artificial blood vessel inner layer having a stent comprising a stainless steel gauze.

5. A method as in claim 1, wherein said providing step comprises providing an artificial blood vessel inner layer having a stent comprising a length of memory metal preprogrammed to expand at a determined temperature.

6. A method as in claim 1, wherein said providing step comprises providing an artificial inner layer having an enclosure comprising a fluid-tight enclosure.

7. A method as in claim 1, wherein said positioning step comprises positioning said artificial inner layer using a catheter.

8. A method as in claim 7, wherein said catheter comprises a guide wire and a sheath.

9. A method as in claim 7, wherein said catheter comprises a blood vessel widener.

10. A method as in claim 9, wherein said widener comprises a cone-shaped element operably attached to a distal end of said catheter.

11. A method as in claim 9, wherein said widener comprises an inflatable balloon operably attached to a distal end of said catheter.

12. A method as in claim 9, wherein said widener is wider than said end section during said inserting step and narrower than said end section after said retaining step due to said stent enclosed within said end section expanding during said expanding step.

13. A method as in claim 9, wherein said widener has substantially the same diameter as an internal diameter of said blood vessel.

14. A method as in claim 9, wherein said retaining step comprises using said widener to widen said stent in order to press said end section against said end flap.

15. A method as in claim 1, wherein said retaining step comprises retaining said end flap by expanding said stent so that an outer diameter of said tubular section is approximately equal to an inner diameter of said blood vessel.

16. A method as in claim 1, wherein the providing step comprises providing an artificial blood vessel inner layer further comprising two end sections creating two enclosures and two stents enclosed within said enclosures.

17. A method as in claim 1, further comprising the step of stitching one end section to said blood vessel.

18. A method as in claim 9, further comprising the step of bunging the blood vessel.

19. A method as in claim 18 wherein said bunging step comprises bunging said blood vessel using said widener.

20. A method as in claim 9, further comprising the step of exerting pressure outwardly on said stent with said widener during a withdrawal of said catheter from said blood vessel.

* * * * *